US012667605B2

(12) United States Patent
Bennis

(10) Patent No.: US 12,667,605 B2
(45) Date of Patent: Jun. 30, 2026

(54) PHARMACEUTICAL COMPOSITION FOR ORAL ADMINISTRATION OF A GLP-1 RECEPTOR AGONIST

(71) Applicant: Farid Bennis, Casablanca (MA)

(72) Inventor: Farid Bennis, Casablanca (MA)

( * ) Notice: Subject to any disclaimer, the term of this patent is extended or adjusted under 35 U.S.C. 154(b) by 105 days.

(21) Appl. No.: 18/279,981

(22) PCT Filed: Feb. 24, 2022

(86) PCT No.: PCT/IB2022/051623
§ 371 (c)(1),
(2) Date: Sep. 1, 2023

(87) PCT Pub. No.: WO2022/185155
PCT Pub. Date: Sep. 9, 2022

(65) Prior Publication Data
US 2024/0156915 A1 May 16, 2024

(30) Foreign Application Priority Data

Mar. 1, 2021 (FR) ...................................... 2101947

(51) Int. Cl.
| *A61K 38/26* | (2006.01) |
| *A61K 9/00* | (2006.01) |
| *A61K 9/20* | (2006.01) |
| *A61K 38/22* | (2006.01) |

(52) U.S. Cl.
CPC ............ *A61K 38/26* (2013.01); *A61K 9/0053* (2013.01); *A61K 9/2009* (2013.01); *A61K 9/2013* (2013.01); *A61K 9/2027* (2013.01); *A61K 9/2054* (2013.01); *A61K 38/22* (2013.01)

(58) Field of Classification Search
None
See application file for complete search history.

(56) References Cited

U.S. PATENT DOCUMENTS 8,309,123 B2 * 11/2012 Bennis ................. A61K 9/2009
424/466
2009/0176691 A1 7/2009 Bennis et al.

FOREIGN PATENT DOCUMENTS

| FR | 2925333 A1 | 6/2009 |
| WO | 2009136392 A2 | 11/2009 |
| WO | 2012080471 A1 | 6/2012 |
| WO | 2017060500 A1 | 4/2017 |
| WO | 2019087083 A2 | 5/2019 |

OTHER PUBLICATIONS

Kalra et al. A Review on Semaglutide: An Oral Glucagon-Like Peptide 1 Receptor Agonist in Management of Type 2 Diabetes Mellitus. Diabetes Ther (2020) 11:1965â1982 (Year: 2020).*
International Search Report issued in PCT/IB2022/051623 dated May 10, 2022 (12 pages).
Written Opinion issued in PCT/IB2022/051623 dated May 10, 2022 (7 pages) non-english.
Minzhi Yu et al., "Battle of GLP-1 delivery technologies", Advanced Drug Delivery Reviews, Elsevier, Amsterdam, NL, vol. 130, No. 15 (Jul. 21, 2018), pp. 113-130.
Weisheng Lu et al., "An orally available hypglycaemic peptide taken up by caveolae transcytosis displays improved hypoglycaemic effects and body weight control in db/db mice", British Journal of Pharmacology, Wiley-Blackwell, UK, vol. 177, No. 15, (Jun. 7, 2020), pp. 3473-3488.

* cited by examiner

*Primary Examiner* — Christina Bradley
(74) *Attorney, Agent, or Firm* — Rothwell, Figg, Ernst & Manbeck, P.C.

(57) ABSTRACT

The invention relates to a pharmaceutical composition for use as a medicament, in the oral treatment of a disease, in particular a metabolic disease, said pharmaceutical composition comprising a Glucagon-like peptide-1 receptor agonist (GLP-1), and a system that can buffer the pH of the pharmaceutical composition to a value ranging from 4 to 8.

37 Claims, No Drawings

Specification includes a Sequence Listing.

PHARMACEUTICAL COMPOSITION FOR ORAL ADMINISTRATION OF A GLP-1 RECEPTOR AGONIST

CROSS REFERENCE TO RELATED APPLICATIONS

This application is a 35 U.S.C. § 371 National Phase Entry Application from PCT/IB2022/051623, filed Feb. 24, 2022, designating the United States, and also claims the benefit of French Application No. 2101947, filed Mar. 1, 2021, the disclosures of which are incorporated herein by reference in their entirety.

TECHNICAL FIELD

The invention relates to a pharmaceutical composition for use as a medicament, in the oral treatment of a disease, said pharmaceutical composition comprising (i) a protein active ingredient, said protein active ingredient being a Glucagon-like peptide-1 receptor agonist (GLP-1), and (ii) a system that can buffer the pH of the pharmaceutical composition to a value ranging from 4 to 8.

PRIOR ART

"Glucagon-like peptide-1" or "GLP-1" is an incretin, that is to say an intestinal hormone secreted by intestinal endocrine cells in response to food intake. GLP-1 modulates glucose homeostasis by binding to the GLP-1 receptor, specific to pancreatic beta cells. The main biological effects of the activation of the GLP-1 receptor are the stimulation of glucose-dependent insulin secretion, inhibition of postprandial glucagon secretion (called glucose-dependent action), the slowing of the gastric emptying, and inhibition of gastric acid secretion (called satietogenic action). The biologically active forms of GLP-1, that is to say GLP-1 (7-36) and GLP-1 (7-37), are obtained after proteolytic cleavage of the initial product GLP-1 (1-37).

GLP-1 has a strong therapeutic interest in the regulation of hyperglycaemia and in the treatment of type 2 diabetes. However, the active forms of GLP-1, that is to say GLP-1 (7-36) and GLP-1 (7-37), have a very short lifespan due to rapid inactivation by the serum enzyme DPP-4 (dipeptyl peptidase 4).

To overcome the constraints related to this inactivation of GLP-1 by DPP-4, two classes of GLP-1 receptor agonists have been developed as medicaments: GLP-1 analogs and exendin 4 analogs (Exenatide). Nevertheless, these GLP-1 receptor agonists remain sensitive to degradation with respect to digestive enzymes, such as pepsin in the stomach and trypsin in the intestine, which has a disadvantage for their administration by oral route.

GLP-1 receptor agonists are therefore administered parenterally. Ozempic® is a medicament in injectable form comprising semaglutide. The Byetta® product is also a medicament that comes in an injectable form and comprises exenatide. However, this administration route is technically restrictive and less comfortable for the patient than the oral route, in particular when the administration is daily. Parenteral administration also poses compliance problems in patients.

The formulations for oral administration of GLP-1 receptor agonists described in the literature generally comprise a compound capable of protecting the GLP-1 receptor agonist from degradation by digestive enzymes. This is the case, for example, of the formulation described in document US 2011/0046053, which is an oral or rectal composition for administering exenatide with a trypsin inhibitor, EDTA and fish oil. The composition comprises a coating which allows to inhibit digestion by the stomach and therefore to protect the protein active ingredient from degradation. Other documents describe the incorporation of a GLP-1 receptor agonist in a polymeric particle (WO 2020/028907), or else the use of minerals such as copper, iron, or zinc in combination with an absorption activator, in order to inhibit proteases and thus prevent degradation by digestive enzymes (WO 2017/060500).

Document WO 2012/080471 describes the use, as a medicament for oral administration, of a solid composition comprising a GLP-1 receptor agonist and a carrier agent called SNAC (or salt of N-(8-(2hydroxybenzoyl)amino) caprylic acid). The SNAC compound allows to protect the GLP-1 receptor agonist by inhibiting the digestive enzymes during passage through the stomach and to improve its absorption. The product Rybelsus® in particular comprises semaglutide, in combination with a SNAC compound and is indicated for oral administration.

However, there remains a need to develop new compositions suitable for oral administration of a GLP-1 receptor agonist which can guarantee optimal protection of the agonist throughout the digestive tract, in particular against digestive enzymes such as pepsin.

SUMMARY OF THE INVENTION

Thus, the present invention, which finds application in the pharmaceutical field, aims at providing a pharmaceutical composition which allows to protect the agonists of the GLP-1 receptor against degradation by digestive enzymes.

According to a first aspect, the invention relates to a pharmaceutical composition for use as a medicament, in the oral treatment of a disease, said pharmaceutical composition comprising (i) a protein active ingredient, said protein active ingredient being a Glucagon-like peptide-1 (GLP-1) agonist, and (ii) a system that can buffer the pH of the pharmaceutical composition to a value ranging from 4 to 8.

According to a second aspect, the invention relates to a method for preparing a composition according to the invention, in which a protein active ingredient is mixed with a system that can buffer the pH of the pharmaceutical composition to a value ranging from 4 to 8, said active protein being a GLP-1 receptor agonist.

According to a third aspect, the invention relates to a kit of reagents, is also called kit-of-parts, for use as a medicament, in the oral treatment of a disease, said kit of reagents comprising:

(i) a pharmaceutical composition in solid form comprising a protein active ingredient, said protein active ingredient being a Glucagon-like peptide-1 receptor agonist (GLP-1), and (ii) a pharmaceutical composition comprising a buffer system, in which said pharmaceutical composition comprising a buffer system (ii) can buffer the pH of the pharmaceutical composition comprising the protein active ingredient (i) to a value ranging from 4 to 8, when the compositions (i) and (ii) are mixed in solution.

DETAILED DESCRIPTION

Definitions

The term "pharmaceutical composition" means a composition suitable for pharmaceutical use. The pharmaceutical composition can comprise one or more pharmaceutically acceptable excipients.

The term "pharmaceutically acceptable excipient" means diluents, adjuvants or carriers, such as preservatives, fillers, disintegrating agents, wetting agents, emulsifying agents, suspending agents, solvents, dispersants, lubricants, antibacterial and antifungal agents, isotonic agents, absorption retardants and their analogues. It is understood that none of these pharmaceutically acceptable excipients is capable of protecting the protein active ingredient against degradation by digestive enzymes in the pharmaceutical composition according to the invention.

The term "oral treatment" means administration via the gastrointestinal tract.

The term "protein active ingredient" denotes an active ingredient consisting of the sequence of amino acid residues bound together by peptide bonds, such as a protein or a peptide.

The term "GLP-1 receptor agonist" designates a protein active ingredient which partially or completely activates the GLP-1 receptor. The GLP-1 receptor agonist "can bind to the GLP-1 receptor, with an affinity constant (Kd) of less than 1 μM, for example 100 nM, and measured using conventional methods, for example described in WO 98/08871. The methods for identifying a GLP-1 receptor agonist may comprise (i) contacting the GLP-1 receptor with a GLP-1 receptor agonist candidate, and (ii) measuring a detectable change in one or more of the biological activities associated with the activation of the GLP-1 receptor. A GLP-1 receptor agonist may be selected from GLP-1, a GLP-1 analog, exendin-4 (also known as "Exenatide") and/or an exendin-4 analog. Preferably, a GLP-1 receptor agonist is (a) GLP-1 or a GLP-1 analog selected from liraglutide, dulaglutide, albiglutide and semaglutide, preferably semaglutide, or (b) exendin-4 or an exendin-4 analog, selected from exenatide and lixisenatide.

The term "GLP-1" corresponds to the GLP-1 (1-37) form, the GLP-1 (7-37) form or the GLP-1 (7-36) form. It may be GLP-1 of human or animal origin, for example GLP-1 of amino acid sequence SEQ ID NO: 1 which corresponds to the (1-37) form of human GLP-1, GLP-1 of amino acid sequence SEQ ID NO: 2 which corresponds to the (7-36) form of human GLP-1, or GLP-1 of amino acid sequence SEQ ID NO: 3 which corresponds to the (7-37) form of human GLP-1.

A "GLP-1 analog" designates a GLP-1 whose amino acid sequence has one or more amino acids substituted by another amino acid and/or one or more deleted amino acids and/or one or more added amino acids. Generally, the GLP-1 analog has at least 90% sequence homology with the corresponding GLP-1. The GLP-1 analog can also comprise one or more amino acids modified, for example by acylation, alkylation, reduction, oxidation or cross-linking. The GLP-1 analog can also be fused to a molecule allowing to increase the half-life of said GLP-1 analog, for example an Fc fragment of an immunoglobulin G, albumin, a fatty acid and/or polyethylene glycol (PEG). The GLP-1 analogue can be selected from liraglutide, dulaglutide, albiglutide and semaglutide, preferentially semaglutide.

Liraglutide corresponds to the (7-37) form of human GLP-1 whose arginine 34 is substituted by a lysine and whose position 26 is modified with a fatty acid of the C16 type.

Dulaglutide is the (7-37) form of human GLP-1 fused to an Fc fragment of IgG4.

Albiglutide results from the fusion of a dimer of (7-36) forms of human GLP-1 with a human albumin. The two (7-36) forms of human GLP-1 of the dimer each have a glycine instead of alanine at position 2.

Semaglutide corresponds to the (7-37) form of human GLP-1 whose positions 8 and 34 have been mutated.

The term "exendin-4" refers to a 39 amino acid protein present in the salivary glands of a giant lizard "the Gila monster". Exenatide is the recombinant or synthetic form of exendin-4. Exenatide is resistant to DPP4 activity.

The term "exendin-4 analog" designates an exendin-4 whose amino acid sequence has one or more amino acids substituted by another amino acid and/or one or more deleted amino acids and/or one or more added amino acids. An exendin-4 analog may also comprise one or more amino acids modified, for example by acylation, alkylation, reduction, oxidation or cross-linking. The exendin-4 analog can also be fused to a molecule allowing to increase the half-life of said exendin-4 analog, for example an Fc fragment of an immunoglobulin G, albumin, a fatty acid and/or polyethylene glycol (PEG). The exendin-4 analog can for example be lixisenatide. Lixisenatide comprises 44 amino acids and corresponds to exendin-4 whose proline 38 is absent and whose 6 lysine residues are added.

The expression "system that can buffer the pharmaceutical composition" in the context of the invention denotes a system capable of exerting a buffering effect on the pharmaceutical composition, in particular in the gastric medium and in the intestinal medium.

The expression "additional compound capable of protecting the protein active ingredient against degradation by digestive enzymes" denotes a compound, other than the system that can buffer the pharmaceutical composition, capable of protecting the protein active ingredient against degradation by digestive enzymes, to prevent the degradation of the protein active ingredient by the digestive enzymes present in the gastric juice and/or the pancreatic juice during the digestion process, such as proteases, preferentially selected from pepsin, trypsin or chymotrypsin, in particular pepsin.

The present invention stems from the surprising advantages demonstrated by the inventors of the effect of a system that can buffer a pharmaceutical composition on the protection of a GLP-1 receptor agonist against degradation by digestive enzymes.

Pharmaceutical Composition

According to a first aspect, the invention relates to a pharmaceutical composition for use as a medicament, in the oral treatment of a disease, said pharmaceutical composition comprising (i) a protein active ingredient, said protein active ingredient being a Glucagon-like peptide-1 (GLP-1) agonist, and (ii) a system that can buffer the pH of the pharmaceutical composition to a value ranging from 4 to 8.

The disease can be a metabolic disease such as type 2 diabetes, non-alcoholic steatohepatitis (called NASH) and/or obesity. Preferably, the disease is type 2 diabetes. In particular, in the context of the treatment of obesity, the composition according to the invention allows to reduce appetite, to induce satiety, which results in a reduction in food intake.

The system that can buffer the pharmaceutical composition allows to obtain a pharmaceutical composition at a pH ranging from 4 to 8, for example at a pH ranging from 4.5 to 7.5, at a pH ranging from 5 to 7, at a pH ranging from 5.5 to 7, to a pH ranging from 6 to 7. Particularly preferably, the system that can buffer the pharmaceutical composition allows to obtain a pharmaceutical composition at a pH ranging from 6.5 to 7.

This system is capable of protecting the protein active ingredient against degradation by digestive enzymes, such as proteases, preferentially selected from pepsin, trypsin or chymotrypsin, in particular pepsin. In the context of the invention, the protection by the system that can buffer the pharmaceutical composition corresponds to an inactivation of the effect of the digestive enzymes in the gastrointestinal environment.

The protection of the protein active ingredient can be measured by a structural analysis of the active ingredient, for example by HPLC. The protection of the protein active ingredient can also be measured by a functional analysis of the active ingredient, for example by measuring the biological activity of the protein active ingredient. The biological activity of the protein active ingredient can be easily determined by looking at its effect on the GLP-1 receptor, for example by implementing a functional test, such as a measurement of the agonist effect on the GLP-1 receptor 1. The measurement of the agonist effect on the GLP-1 receptor can for example be carried out on hamster kidney cells by measuring the production of cyclic AMP.

In the examples of the present application, the protection of the protein active ingredient is measured by HPLC.

The amount of protein active ingredient present in the composition according to the invention, namely of the GLP-1 receptor agonist, can be adjusted by the person skilled in the art of the disease to be treated. The pharmaceutical composition according to the invention may comprise from 0.0001 to 5% by mass of the GLP-1 receptor agonist relative to the total mass of the pharmaceutical composition, preferably from 0.001 to 1.5%, preferably from 0.001 to 1% by mass of the GLP-1 receptor agonist, more preferably from 0.01 to 0.5%, even more preferably from 0.05 to 0.5% by mass of the GLP-1 receptor agonist, for example 0.08%, 0.2%, 0.4%, 0.7% or 1.4% by mass of the GLP-1 receptor agonist. For example, the pharmaceutical composition according to the invention comprises 0.08%, 0.2%, 0.4%, 0.7% or 1.4% by mass of semaglutide relative to the total mass of the pharmaceutical composition.

Advantageously, the system is capable of protecting at least 70% of the protein active ingredient (by a structural or functional analysis) from degradation by at least one digestive enzyme when the pharmaceutical composition is contacted with said digestive enzyme(s), for example at least 75%, at least 80%, at least 85%, at least 90%, at least 95%. A protection of 100% of the protein active ingredient corresponds to a protein active ingredient which has not undergone any degradation and which has retained all of its biological activity. A protection of 70% of the protein active ingredient corresponds to a 30% degraded active ingredient, that is to say that, in a composition comprising the protein active ingredient, 70% of the protein active ingredient is not degraded and 30% of the protein active ingredient is degraded. A protection of 0% of the protein active ingredient corresponds to an active ingredient that is totally degraded and has lost all of its biological activity. Advantageously, the system is capable of protecting at least 70%, at least 80%, at least 90% of the protein active ingredient from degradation by pepsin, for example when the pharmaceutical composition is contacted with 2 to 5 mg/mL of pepsin, for example 3.2 mg/mL of pepsin, for one hour or for two hours.

The system that can buffer the pharmaceutical composition can be selected from the list of buffer systems given in the European Pharmacopoeia, current edition (monograph 4.1.3). Preferably, the system that can buffer the pharmaceutical composition according to the invention is selected from the following buffers: phosphate, acetate, maleate, phthalate, succinate, citrate, such as anhydrous monosodium citrate, imidazole, tetrabutylammonium, trihydroxymethyl-aminomethane, tris-glycine, bicarbonate such as sodium bicarbonate, barbitol, tris-EDTA BSA, copper and zwitteri-onic sulfate. The system that can buffer the pharmaceutical composition advantageously comprises a phosphate buffer, such as monosodium phosphate dihydrate, a citrate buffer, such as anhydrous monosodium citrate, and a bicarbonate buffer, such as sodium bicarbonate. In a particular embodiment, the system that can buffer the pharmaceutical composition consists of a phosphate buffer, such as monosodium phosphate dihydrate, a citrate buffer, such as anhydrous monosodium citrate, and a bicarbonate buffer, such as sodium bicarbonate.

The pharmaceutical composition according to the invention may comprise from 5 to 99% by mass of system that can buffer the composition relative to the total mass of the pharmaceutical composition, preferably from 10 to 80%, in particular from 20 to 50%, for example 30%, 35%, 40%, 45%, 55%, 60%, 65%, 70%, 75%, 80% by mass of system that can buffer the composition relative to the total mass of the pharmaceutical composition. In another embodiment of the invention, the pharmaceutical composition according to the invention may comprise from 50 to 99% by mass of system that can buffer the composition relative to the total mass of the pharmaceutical composition, preferably from 70 to 99%, in particular from 80 to 99%, for example 85%, 90%, 95% 98% by mass of system that can buffer the composition relative to the total mass of the pharmaceutical composition.

In a particular embodiment, the system that can buffer the pharmaceutical composition comprises:

(i) from 0.5 to 20% by mass of monosodium phosphate dihydrate relative to the total mass of the system that can buffer the pharmaceutical composition, preferably from 1 to 15%, more preferably from 2 to 10% by mass of monosodium phosphate dihydrate relative to the total mass of the system that can buffer the pharmaceutical composition, (ii) from 10 to 60% by mass of anhydrous monosodium citrate with respect to the total mass of the system that can buffer the pharmaceutical composition, preferably from 20 to 50%, more preferably from 30 to 45% by mass of anhydrous monosodium citrate with respect to the total mass of the system that can buffer the pharmaceutical composition, and (iii) from 20 to 95% by mass of sodium bicarbonate relative to the total mass of the system that can buffer the pharmaceutical composition, preferably from 40 to 80%, more preferably from 50 to 70% by mass of sodium bicarbonate relative to the total mass of the system that can buffer the pharmaceutical composition.

In a very particular embodiment, the system that can buffer the pharmaceutical composition comprises:

(i) about 5% by mass of monosodium phosphate dihydrate relative to the total mass of the system that can buffer the pharmaceutical composition, (ii) about 35% by mass of anhydrous monosodium citrate relative to the total mass of the system that can buffer the composition, and (iii) about 60% by mass of sodium bicarbonate relative to the total mass of the system that can buffer the pharmaceutical composition.

According to a preferred embodiment, the pharmaceutical composition is free of additional compound capable of protecting the protein active ingredient against degradation by digestive enzymes. In this embodiment, the system that can buffer the pH of the pharmaceutical composition to a value ranging from 4 to 8 is therefore the only compound present in the pharmaceutical composition having the ability to protect the protein active ingredient against degradation by digestive enzymes. In particular, the pharmaceutical composition according to the invention does not comprise a physical protection system such as a coating, a matrix, a capsule wall, such as a liposome enveloping the protein active ingredient and protecting it from degradation by digestive enzymes. In particular, the pharmaceutical composition according to the invention is free of compound capable of inhibiting the action of digestive enzymes, such as for example a mineral, a SNAC compound, pepstatin, a diazoketone, an alginate and/or a soy extract.

Preferably, the composition according to the invention does not comprise any other protein active ingredient(s), such as insulin, one of its derivatives or one of its analogues.

The composition can be in solid or liquid form.

When the composition is in solid form, it comprises a system that can buffer the pharmaceutical composition when it is dissolved, for example in the stomach after taking the pharmaceutical composition according to the invention orally. A solid composition can for example be in the form of tablets, in particular dispersible, orodispersible, effervescent tablets, pills, a powder, an effervescent powder, granules, effervescent granules or a lyophilisate. Preferably, the composition is in an effervescent form, advantageously in the form of effervescent tablets.

In a particular embodiment and when the composition is in solid form, the system that can buffer the pharmaceutical composition comprises:

(i) from 0.5 to 20% by mass of monosodium phosphate dihydrate relative to the total mass of the pharmaceutical composition, preferably from 1 to 15%, more preferably from 2 to 10% by mass of monosodium phosphate dihydrate relative to the total mass of the pharmaceutical composition, (ii) from 10 to 60% by mass of anhydrous monosodium citrate relative to the total mass of the pharmaceutical composition, preferably from 20 to 50%, more preferably from 30 to 45% by mass of anhydrous monosodium citrate relative to the total mass of the pharmaceutical composition, and (iii) from 20 to 95% by mass of sodium bicarbonate relative to the total mass of the system that can buffer the pharmaceutical composition, preferably from 40 to 80%, more preferably from 50 to 70% by mass of sodium bicarbonate relative to the total mass of the pharmaceutical composition.

In a very specific embodiment and when the composition is in solid form, the system that can buffer the pharmaceutical composition comprises:

(i) about 3.5% by mass of monosodium phosphate dihydrate relative to the total mass of the pharmaceutical composition, (ii) about 32% by mass of anhydrous monosodium citrate relative to the total mass of the pharmaceutical composition, and (iii) about 59% by mass of sodium bicarbonate relative to the total mass of the pharmaceutical composition.

In a very preferred embodiment of the invention and when the composition is in solid form, the pharmaceutical composition according to the invention comprises:

(i) from 0.5 to 20% by mass of monosodium phosphate dihydrate relative to the total mass of the pharmaceutical composition, preferably from 1 to 15%, more preferably from 2 to 10% by mass of monosodium phosphate dihydrate relative to the total mass of the pharmaceutical composition, for example 3.5%, (ii) from 10 to 60% by mass of anhydrous monosodium citrate relative to the total mass of the pharmaceutical composition, preferably from 20 to 50%, more preferably from 30 to 45% by mass of anhydrous monosodium citrate relative to the total mass of the pharmaceutical composition, for example 32%, (iii) from 20 to 95% by mass of sodium bicarbonate relative to the total mass of the system that can buffer the pharmaceutical composition, preferably from 40 to 80%, more preferably from 50 to 70% by mass of sodium bicarbonate relative to the total mass of the pharmaceutical composition, for example 59%, (iv) from 0.5 to 20% by mass of sodium benzoate relative to the total mass of the pharmaceutical composition, preferably from 1 to 10%, more preferably from 2 to 5% by mass of sodium benzoate relative to the total mass of the pharmaceutical composition, for example 4.5%, and (v) from 0.0001 to 5% by mass of the GLP-1 receptor agonist, preferably semaglutide, relative to the total mass of the pharmaceutical composition, preferably from 0.001 to 1.5%, preferably from 0.001 to 1%, more preferably from 0.01 to 0.5%, even more preferably from 0.05 to 0.5% by mass of the GLP-1 receptor agonist relative to the total mass of the pharmaceutical composition, for example 0.08%, 0.2%, 0.4%, 0.7% or 1.4% by mass of the GLP-1 receptor agonist.

In a preferred embodiment of the invention and when the composition is in solid form, for example in the form of an effervescent tablet, the pharmaceutical composition according to the invention comprises:

(i) 120 milligrams (mg) of monosodium phosphate dihydrate, (ii) 1142 mg of anhydrous monosodium citrate, (iii) 2076 mg of sodium bicarbonate, (iv) 157 mg of sodium benzoate, and (v) from 0.5 to 100 mg, preferably from 0.5 to 40 mg, more preferably from 1 to 50 mg, more preferably 3, 7, 14, 25 or 50 mg of a GLP-1 receptor agonist, preferably semaglutide.

Given that the pharmaceutical composition may be free of additional compound capable of protecting the protein active ingredient against degradation by digestive enzymes, when the pharmaceutical composition according to the invention is in solid form, it does not have enteric coating.

When the composition is in liquid form, it can be in the form of a solute, a suspension or a syrup.

The pharmaceutical composition may comprise one or more pharmaceutically acceptable excipients, which suits the form of the composition selected.

The composition according to the invention may separately comprise a protein active ingredient and a system that can buffer the pharmaceutical composition. In this embodiment, the protein active ingredient and the system that can buffer the pharmaceutical composition are administered jointly so that the composition according to the invention is buffered when the protein active is ingredient passes through the digestive system.

In a particular embodiment, the composition for use according to the invention is prepared from (i) a system that can buffer the pharmaceutical composition in the form of an effervescent tablet and (ii) a protein active ingredient in the form of tablet, for example an effervescent tablet. The two tablets are then mixed in solution to form the composition for use according to the invention.

According to another embodiment, the composition according to the invention can be formulated in unit form, namely the protein active ingredient and the system that can buffer the pharmaceutical composition are formulated together.

Method

According to a second object, the invention relates to a method for preparing a pharmaceutical composition according to the invention, in which a protein active ingredient is mixed with a system that can buffer the pH of said pharmaceutical composition to a value ranging from 4 to 8, said protein active ingredient being a GLP-1 Glucagon-like peptide-1 receptor agonist (GLP-1).

The preparation of such a composition is carried out according to the conventional methods described in the literature. A particular mode of preparation of a pharmaceutical composition according to the invention is detailed in the examples.

The preparation of a pharmaceutical composition in solid or liquid form is carried out using conventional methods, described in the literature.

The preparation of a composition in solid form comprises mixing a protein active ingredient selected from GLP-1 receptor agonists and a system that can buffer the pH of said pharmaceutical composition to a value ranging from 4 to 8. The buffer system will then be capable of buffering the composition in solid form when it is dissolved, for example in the stomach after taking the pharmaceutical composition according to the invention orally.

The features of the pharmaceutical composition as described above, in particular in the "pharmaceutical composition" part, are applicable to the method is according to the invention.

Kit of Reagents (or Kit-of-Parts)

According to a third object, the invention relates to a kit of reagents, also called kit-of-parts, for use as a medicament, in the oral treatment of a disease, said kit of reagents comprising:
(i) a pharmaceutical composition in solid form comprising a protein active ingredient, said protein active ingredient being a Glucagon-like peptide-1 receptor agonist (GLP-1), and
(ii) a pharmaceutical composition comprising a buffer system, in which said pharmaceutical composition comprising a buffer system (ii) can buffer the pH of the pharmaceutical composition comprising the protein active ingredient (i) to a value ranging from 4 to 8, when the compositions (i) and (ii) are mixed in solution.

The disease can be a metabolic disease such as type 2 diabetes, non-alcoholic steatohepatitis (called NASH for non-alcoholic steatohepatitis) and/or obesity. Preferably, the disease is type 2 diabetes. In particular, in the context of the treatment of obesity, the kit of reagents (or kit-of-parts) according to the invention allows to reduce appetite, to induce satiety, which results in a decrease in food intake.

In the context of the kit of reagents according to the invention, the pharmaceutical composition comprising a buffer system (ii) can buffer the pH of the pharmaceutical composition comprising the protein active ingredient (i) to a value ranging from 4 to 8, when the compositions (i) and (ii) are mixed in solution, for example to a value ranging from 4.5 to 7.5, to a value ranging from 5 to 7, to a value ranging from 5.5 to 7, to a value ranging from 6 to 7. Particularly preferably, the pharmaceutical composition comprising a buffer system (ii) can buffer the pH of the pharmaceutical composition comprising the protein active ingredient (i) to a value ranging from 6.5 to 7, when the compositions (i) and (ii) are mixed in solution.

The buffer system of the pharmaceutical composition (ii) of the kit of reagents, when mixed in solution with the pharmaceutical composition (i), is capable of protecting the protein active ingredient of the pharmaceutical composition (i) against a degradation by digestive enzymes, such as proteases, preferably selected from pepsin, trypsin or chymotrypsin, in particular pepsin. In the context of the invention, the protection by the buffer system of the pharmaceutical composition (ii) corresponds to an inactivation of the effect of the digestive enzymes in the gastrointestinal medium on the protein active ingredient of the pharmaceutical composition (i).

Once the compositions (i) and (ii) of the kit of reagents are mixed in solution, the protection of the protein active ingredient can be measured in the same way as for the pharmaceutical composition according to the invention, for example by HPLC.

The compositions (i) and (ii) of the kit of reagents can be mixed in solution in the stomach after taking the pharmaceutical compositions (i) and (ii) separately orally. Alternatively, the compositions (i) and (ii) can be mixed in solution before being taken orally.

Advantageously, the buffer system of the pharmaceutical composition (ii), when it is mixed in solution with the pharmaceutical composition (i), is capable of protecting at least 70% of the protein active ingredient of the pharmaceutical composition (i) (by a structural or functional analysis) from degradation by at least one digestive enzyme when the solution comprising compositions (i) and (ii) is contacted with said digestive enzyme(s), for example at least 75%, at least 80%, at least 85%, at least 90%, at least 95%. A protection of 100% of the protein active ingredient corresponds to a protein active ingredient which has not undergone any degradation and which has retained all of its biological activity. A protection of 70% of the protein active ingredient corresponds to an active ingredient degraded to 30%, that is to say that, in a pharmaceutical composition (ii) comprising the protein active ingredient, 70% of the protein active ingredient is not degraded and 30% of the active protein principle is degraded. A protection of 0% of the protein active ingredient corresponds to an active ingredient that is totally degraded and has lost all of its biological activity. Advantageously, the buffer system is capable of protecting at least 70%, at least 80%, at least 90% of the protein active ingredient from degradation by pepsin, for example when the solution comprising compositions (i) and (ii) is contacted with 2 to 5 mg/mL of pepsin, for example 3.2 mg/mL of pepsin, for one hour or for two hours.

When the pharmaceutical composition (i) of the kit of reagents is in solid form, it may for example be in the form of tablets, in particular dispersible, orodispersible, effervescent tablets, pills, a powder, an effervescent powder, granules, effervescent granules or a lyophilisate, advantageously in the form of effervescent tablets.

When the pharmaceutical composition (i) of the kit of reagents is in solid form, it may comprise from 0.5 to 100 mg of a GLP-1 receptor agonist, preferably from 0.5 to 40 mg of a GLP-1 receptor agonist, more preferably 1 to 50 mg, more preferably 3, 7, 14, 25 or 50 mg of a GLP-1 receptor agonist. For example, the pharmaceutical composition (i) comprises 3, 7, 14, 25 or 50 mg of semaglutide.

The pharmaceutical composition (i) of the kit of reagents may comprise one or more pharmaceutically acceptable excipients, which is suitable for the solid form.

An example of pharmaceutical composition (i) that can be used in the context of the kit of reagents according to the invention corresponds to the commercial product Rybelsus®.

The buffer system of the pharmaceutical composition (ii) of the kit of reagents can be selected from the list of buffer systems given in the European Pharmacopoeia, current edition (monograph 4.1.3). Preferably, the buffer system of the pharmaceutical composition (ii) is selected from the following buffers: phosphate, acetate, maleate, phthalate, succinate, citrate, such as anhydrous monosodium citrate, imidazole, tetrabutylammonium, trihydroxymethylaminomethane, tris-glycine, bicarbonate such as sodium bicarbonate, barbitol, tris-EDTA BSA, copper and zwitterionic sulfate. The buffer system of the pharmaceutical composition (ii) advantageously comprises a phosphate buffer, such as monosodium phosphate dihydrate, a citrate buffer, such as anhydrous monosodium citrate, and a bicarbonate buffer, such as sodium bicarbonate. In a particular embodiment, the buffer system of the pharmaceutical composition (ii) consists of a phosphate buffer, such as monosodium phosphate dihydrate, a citrate buffer, such as anhydrous monosodium citrate, and a bicarbonate buffer, such as sodium bicarbonate.

In a particular embodiment, the buffer system of the pharmaceutical composition (ii) of the kit of reagents comprises:

(i) from 0.5 to 20% by mass of monosodium phosphate dihydrate relative to the total mass of the buffer system of the pharmaceutical composition (ii), preferably from 1 to 15%, more preferably from 2 to 10% by mass of monosodium phosphate dihydrate relative to the total mass of the buffer system of the pharmaceutical composition (ii), (ii) from 10 to 60% by mass of anhydrous monosodium citrate relative to the total mass of the buffer system of the pharmaceutical composition (ii), preferably from 20 to 50%, more preferably from 30 to 45% by mass of anhydrous monosodium citrate relative to the total mass of the buffer system of the pharmaceutical composition (ii), and (iii) from 20 to 95% by mass of sodium bicarbonate relative to the total mass of the buffer system of the pharmaceutical composition (ii), preferably from 40 to 80%, more preferably from 50 to 70% by mass of sodium bicarbonate relative to the total mass of the buffer system of the pharmaceutical composition (ii).

In a very particular embodiment, the buffer system of the pharmaceutical composition (ii) comprises:

(i) about 5% by mass of monosodium phosphate dihydrate relative to the total mass of the buffer system of the pharmaceutical composition (ii), (ii) about 35% by mass of anhydrous monosodium citrate relative to the total mass of the buffer system of the pharmaceutical composition (ii), and (iii) about 60% by mass of sodium bicarbonate relative to the total mass of the buffer system of the pharmaceutical composition (ii).

The pharmaceutical composition (ii) of the kit of reagents can be in solid or liquid form.

When the pharmaceutical composition (ii) of the kit of reagents is in is solid form, it may for example be in the form of tablets, which are in particular dispersible, orodispersible, effervescent, pills, a powder, an effervescent powder, granules, effervescent granules or a lyophilisate. Preferably, the pharmaceutical composition (ii) is in an effervescent form, advantageously in the form of effervescent tablets.

When the pharmaceutical composition (ii) of the kit of reagents is in solid form, for example in the form of an effervescent tablet, it preferably comprises:

(i) 120 milligrams (mg) of monosodium phosphate dihydrate, (ii) 1142 mg anhydrous monosodium citrate, (iii) 2076 mg sodium bicarbonate, and (iv) 157 mg sodium benzoate.

When the pharmaceutical composition (ii) of the kit of reagents is in liquid form, it may be in the form of a solute, a suspension or a syrup.

The pharmaceutical composition (ii) of the kit of reagents may comprise one or more pharmaceutically acceptable excipients, which suits the form of the composition (ii) selected.

Preferably the pharmaceutical composition (i) and the pharmaceutical composition (ii) are in solid form, for example in the form of effervescent tablets.

According to a preferred embodiment, the kit of reagents (or kit-of-parts) according to the invention is free of additional compound capable of protecting the protein active ingredient of the pharmaceutical composition (i) against a degradation by digestive enzymes. In particular, the composition (i) and the composition (ii) are free of additional compound capable of protecting the protein active ingredient of the pharmaceutical composition (i) against degradation by digestive enzymes. In this embodiment, the buffer system of the pharmaceutical composition (ii) is the only compound present in the kit of reagents according to the invention having the capacity to protect the protein active ingredient of the pharmaceutical composition (i) against degradation by digestive enzymes. In particular, the pharmaceutical composition (i) comprising a protein active ingredient and the pharmaceutical composition (ii) comprising a buffer system do not comprise a physical protection system such as a coating, a matrix, a capsule wall, such as a liposome enveloping the protein active ingredient and protecting it from degradation by digestive enzymes. In particular, the pharmaceutical composition (i) comprising a protein active ingredient and the pharmaceutical composition (ii) comprising a buffer system are free of compound capable of inhibiting the action of digestive enzymes, such as for example a mineral, a SNAC compound, pepstatin, a diazoketone, an alginate and/or a soy extract.

Preferably, the pharmaceutical composition (i) of the kit of reagents comprising a protein active ingredient and the pharmaceutical composition (ii) comprising a buffer system do not comprise other protein active ingredient(s), such as insulin, one of its derivatives or one of its analogues.

Since the pharmaceutical compositions (i) and (ii) of the kit of reagents can be free of additional compound capable of protecting the protein active ingredient against degradation by digestive enzymes, when either one of the pharmaceutical compositions (i) and (ii) are in solid form, they do not have an enteric coating.

EXAMPLES

Example 1: Preparation of a System That Can Buffer a Pharmaceutical Composition According to the Invention

Example 1A

A preparation in the form of effervescent tablets comprising a buffer system was prepared according to Table 1.

Step 1) The sodium hydrogen carbonate, the anhydrous monosodium citrate, and the monosodium phosphate dihydrate were dry mixed.

Step 2) The mixture obtained in step 1) was granulated using a wetting solution composed of water and 96% ethanol.

Step 3) The granules thus obtained were calibrated and then dried until a predetermined residual humidity was obtained.

Step 4) The granules were mixed with sodium benzoate.

Step 5) The final mixture was compressed in order to obtain a is predetermined hardness, breaking strength, diameter and mass.

The GLP-1 receptor agonist can be formulated separately then mixed extemporaneously with the tablet once the tablet is dissolved or incorporated directly into the tablet as detailed in Example 1B. The tablet can thus be incorporated into a GLP-1 receptor agonist of choice.

Table 1 shows the composition of the effervescent tablets thus prepared.

TABLE 1

| Ingredients | Amount in mg/tablet |
|---|---|
| Sodium hydrogen carbonate (also called sodium bicarbonate) | 2076.0 |
| Anhydrous monosodium citrate | 1142.0 |
| Sodium benzoate | 157.2 |
| Monosodium phosphate dihydrate | 120.0 |
| 96% ethanol (evaporated during the drying step) | QS granulation |
| Purified water (evaporated during the drying step) | QS granulation |
| Total | 3495.6 (i.e. 3.5 g) |

Example 1B

A preparation in the form of effervescent tablets comprising a buffer system was prepared according to Table 2.

Step 1) Sodium hydrogen carbonate, anhydrous monosodium citrate, and the monosodium phosphate dihydrate were dry mixed.

Step 2) The mixture obtained in step 1) was granulated using a wetting solution composed of water and 96% ethanol.

Step 3) The granules thus obtained were calibrated then dried until a predetermined residual humidity was obtained.

Step 4) Granules were mixed with a semaglutide content of 3 mg, 7 mg, or 14 mg and sodium benzoate.

Step 5) The final mixture was compressed to obtain tablets which have is a predetermined hardness, breaking strength, diameter and mass.

Table 2 shows the composition of the effervescent tablets thus prepared.

TABLE 2

| Ingredients | Amount in mg/tablet |
|---|---|
| Sodium hydrogen carbonate (also called sodium bicarbonate) | 2076.0 |
| Anhydrous monosodium citrate | 1142.0 |
| Sodium benzoate | 157.2 |
| Monosodium phosphate dihydrate | 120.0 |
| Semaglutide | 3.0 to 14.0 |
| 96% ethanol (evaporated during the drying step) | QS granulation |
| Purified water (evaporated during the drying step) | QS granulation |
| Total | 3495.6 (i.e. 3.5 g) |

Example 2: Measurement of the Protection of Semaglutide With a Composition According to the Invention, Under Gastric Conditions Reproduced In Vitro (Acid pH and Addition of Pepsin)

The purpose of this test is to show the gastric stability of semaglutide in a composition according to the invention.

Step 1) The tablet obtained in Example 1A was dissolved in 50 mL of drinking water in order to obtain a buffered solution.

Step 2) The simulated gastric medium was prepared with hydrochloric acid (0.2 N HCl), adjusting the pH to 1.2.

Step 3) The buffered solution obtained in step 1) was mixed with 50 ml of simulated gastric medium, in order to obtain a final solution of 100 ml with 0.1 N HCL.

Step 4) Semaglutide was added to the solution obtained in step 3), in is order to obtain a final concentration of semaglutide of 0.05 mg/ml.

Step 5) Pepsin was added to the solution obtained in step 4) at a final concentration of 3.2 mg/ml or without addition of pepsin (without pepsin), and the solution obtained was kept under constant stirring at 37° C. for 2 hours.

The semaglutide assay was performed by ultra-high performance liquid chromatography (UHPLC) coupled to an ultraviolet (UV) detector using an external standard calibration. The residual semaglutide content was calculated by measuring the semaglutide content at time t relative to the initial semaglutide content. The result is a ratio expressed in percent (%). The residual content of semaglutide corresponds to the protection percentage of semaglutide.

TABLE 3

| | Semaglutide residual content (%) | | | |
|---|---|---|---|---|
| | Simulated gastric medium at pH 1.2 (without pepsin) | | Simulated gastric medium at pH 1.2 with pepsin (3.2 mg/ml) | |
| Solution comprising semaglutide and without buffer system | T 0 h 100% | T 2 h 100% | T 0 h 0% | T 2 h 0% |

TABLE 4

| | Semaglutide residual content (%) | | | |
|---|---|---|---|---|
| | Simulated gastric medium at pH 1.2 (without pepsin) | | Simulated gastric medium at pH 1.2 with pepsin (3.2 mg/ml) | |
| Solution comprising semaglutide and the buffered solution | T 0 h 103.5% | T 2 h 104.1% | T 0 h 104.6% | T 2 h 105.2% |

Results

The results described in Tables 3 and 4 show that semaglutide was not protected in an acid medium in the presence of pepsin when it was not formulated in a composition according to the invention (0% residual content with pepsin and without a buffer system). When the semaglutide was formulated with a buffer system according to the invention, the semaglutide was not degraded after 2 hours with and without pepsin.

These results show that the composition according to the invention confers total protection of semaglutide against degradation by pepsin in a simulated gastric medium.

Example 3: Measurement of the Protection of Exenatide With a Composition According to the Invention, Under Gastric Conditions Reproduced In Vitro (Acid pH and Addition of Pepsin)

Step 1) An effervescent tablet (according to Example 1A) was dissolved in 50 mL of drinking water in order to obtain a buffered solution.

Step 2) The simulated gastric medium was prepared with hydrochloric acid (0.2 N HCl), adjusting the pH to 1.2.

Step 3) The buffered solution obtained in step 1) was mixed with 50 ml of simulated gastric medium, in order to obtain a final solution of 100 ml with 0.1 HCL.

Step 4) The exenatide was then added to the solution obtained in step 3) in order to obtain a final concentration of 0.05 mg/mL (5 mg of exenatide in final 100 mL) or 1 mg/mL (5 mg of exenatide in final 5 mL) in the final solution. The solution was mixed to solubilize the exenatide and homogenize the solution.

Step 5) Pepsin was then added to the solution at the conventional dose of 3.2 mg/mL or without added pepsin (without pepsin). The solution was kept under constant stirring at 37° C. for 2 hours.

Exenatide content was specifically measured by high performance liquid chromatography (HPLC). The residual content was calculated by measuring the exenatide content at a time t relative to the initial exenatide content. The result is a ratio expressed in percent (%). The residual level of exenatide corresponds to the protection percentage of the exenatide.

16

Results

The results are shown in Tables 5 and 6. The exenatide was protected by the system that can buffer the pharmaceutical composition in the presence of pepsin. The composition according to the invention also allowed to protect exenatide in the absence of pepsin (Table 5). However, when exenatide was introduced alone (without a buffer system) in gastric medium with pepsin, exenatide was completely degraded (Table 6). These results show the protective effect of the buffer system on exenatide in gastric conditions and in the presence of pepsin.

Example 4: Measurement of the Protection of Semaglutide With a Composition According to the Invention Compared to the Product Rybelsus®, Under Gastric Conditions Reproduced In Vitro (Acid pH and Addition of Pepsin)

The gastro-resistance tests with semaglutide were carried out at a concentration of 0.05 mg/mL (5 mg of semaglutide in final 100 mL). The simulated gastric medium was prepared following the same protocol as that described in Example 3.

The product Rybelsus® comprises Semaglutide, Sodium Salcaprozate (SNAC), Povidone, Microcrystalline Cellulose, and Magnesium Stearate.

Step 1) A 14 mg Rybelsus® tablet was used for the comparative tests and was dissolved in 50 mL of drinking water for thirty minutes with stirring. The final semaglutide concentration was 0.28 mg/mL.

Step 2) An effervescent tablet (according to Example 1A) was added or not to the solution obtained in step 1. After cessation of effervescence, 50 ml of 0.2 N HCL at pH 1.2 were added to obtain a final solution of 100 ml of 0.1 N HCL, which corresponds to the simulated gastric environment. The final concentration of semaglutide is 14 mg per 100 mL.

TABLE 5

| | Residual content of exenatide in percent (%) | | |
|---|---|---|---|
| Conditions | Mixture comprising the simulated gastric medium (pH 1.2 with pepsin (3.2 mg/mL)) and the buffered solution comprising 0.05 mg/mL exenatide | Mixture comprising the simulated gastric medium (pH 1.2, with pepsin (3.2 mg/mL)) and the buffered solution comprising 1 mg/mL exenatide | Mixture comprising the simulated gastric medium (pH 1.2 without pepsin) and the buffered solution comprising 0.05 mg/mL of exenatide |
| T = 0 h | N/A | N/A | N/A |
| T = 1 h | 94.1% | 98.6% | — |
| T = 2 h | 92.8% | 97.8% | 116% |

TABLE 6

| | Residual content of exenatide in percent (%) | |
|---|---|---|
| Conditions | Mixture comprising the simulated gastric medium (pH 1.2 without pepsin) and the solution comprising exenatide (without buffer system) | Mixture comprising the simulated gastric medium (pH 1.2, with pepsin (3.2 mg/mL)) and the solution comprising exenatide (without buffer system) |
| T = 0 h | 100% | 0% |
| T = 2 h | 100% | 0% |

Step 3) The pepsin was then added or not to the solution obtained in step 2, at the conventional dose of 3.2 mg/ml. The test was carried out for 2 hours at a temperature of 37° C.

The semaglutide content was specifically assayed by high performance liquid chromatography (HPLC). The residual content was calculated by measuring the semaglutide content at time t relative to the initial semaglutide content. The result is a ratio expressed in percent (%). The residual content of semaglutide corresponds to the percentage of protection of the semaglutide.

TABLE 7

| Residual semaglutide content in percent (%) | | |
|---|---|---|
| Mixture comprising the simulated gastric medium (pH 1.2 with pepsin (3.2 mg/mL mg/mL)) and the buffered solution comprising 0.05 mg/ml of semaglutide | Mixture comprising the simulated gastric medium (pH 1.2 without pepsin) and the buffered solution comprising 0.05 mg/mL of semaglutide | |
| T = 0 h | N/A | N/A |
| T = 1 h | 104.6% | 103.5% |
| T = 2 h | 105.2% | 104.1% |

TABLE 8

| Residual semaglutide content in percent (%) | | |
|---|---|---|
| Mixture comprising the simulated gastric medium (pH 1.2 without pepsin) and the solution comprising Rybelsus (without buffer system) | Mixture comprising the simulated gastric medium (pH 1.2 with pepsin) and the solution comprising Rybelsus (without buffer system) | Mixture comprising the simulated gastric medium (pH 1.2, with pepsin), buffered solution and the solution comprising Rybelsus |
| T = 0 h N/A | N/A | N/A |
| T = 1 h 78.6% | 0% | 102.8% |
| T = 2 h 16.2% | 0% | 96.8% |

Results

The results show complete protection of semaglutide in simulated gastric medium in the presence of pepsin and with the buffer system (Table 7). In the absence of pepsin, semaglutide is also stable in the presence of the buffer system (Table 7). The results show that in the absence of pepsin, Rybelsus is only stable at a level of 78% for 1 hour in gastric medium and is only maintained at a level of 16% after 2 hours (Table 8). The semaglutide formulated in Rybelsus is completely and immediately degraded by pepsin in a simulated gastric medium and without a buffer system (Table 8). Thus, the pharmaceutical composition of the invention allows to protect the product Rybelsus from acidity in the gastric medium and from pepsin.

| Sequence listing: | | |
|---|---|---|
| SEQ ID NO: 1 | Human GLP-1 | HDEFERHAEGTFTSDVSSYLEGQAAKEFIAWLVK GRG |
| SEQ ID NO: 2 | Human GLP-1 (7-36) | HAEGTFTSDVSSYLEGQAAKEFIAWLVKGR |
| SEQ ID NO: 3 | Human GLP-1 (7-37) | HAEGTFTSDVSSYLEGQAAKEFIAWLVKGRG |

The invention claimed is:

1. A method for the oral treatment of a disease, comprising administering a pharmaceutical composition, said pharmaceutical composition comprising:
(i) a protein active ingredient selected from the group consisting of GLP-1, semaglutide, liraglutide, dulaglutide, albiglutide, exenatide, and lixisenatide, and
(ii) a system that can buffer the pH of the pharmaceutical composition to a value ranging from 4 to 8, wherein the system that can buffer the pharmaceutical composition comprises:
  (a) from 0.5 to 20% by mass monosodium phosphate dihydrate relative to the total mass of the pharmaceutical composition,
  (b) from 10 to 60% by mass anhydrous monosodium citrate relative to the total mass of the pharmaceutical composition,
  (c) from 20 to 95% by mass sodium bicarbonate relative to the total mass of the system that can buffer the pharmaceutical composition, and
  (d) from 0.5 to 20% by mass sodium benzoate relative to the total mass of the pharmaceutical composition.

2. The method of treatment according to claim 1, wherein the protein active ingredient is selected from the group consisting of GLP-1, semaglutide, liraglutide, dulaglutide, and albiglutide.

3. The method of treatment according to claim 1, wherein the disease is a metabolic disease.

4. The method of treatment according to claim 1, wherein the protein active ingredient selected from exenatide and lixisenatide.

5. The method of treatment according to claim 1, wherein the composition is in liquid form or in solid form.

6. The method of treatment according to claim 1, wherein the pharmaceutical composition is free of additional compound(s) capable of protecting the protein active ingredient against degradation by digestive enzymes.

7. The method of treatment according to claim 1, wherein the system that can buffer the pharmaceutical composition allows to obtain a pH ranging from 4.5 to 7.5.

8. The method of treatment according to claim 1, wherein the system that can buffer the pharmaceutical composition is capable of protecting at least 70% of the protein active ingredient from degradation by at least one digestive enzyme when the pharmaceutical composition is contacted with said digestive enzyme(s).

9. The method of treatment according to claim 1, wherein the system that can buffer the pharmaceutical composition is capable of protecting at least 70% of the protein active ingredient from degradation by pepsin when the pharmaceutical composition is contacted with 2 to 5 mg/ml of pepsin for one hour.

10. The method of treatment according to claim 1, wherein the composition does not comprise insulin, a derivative thereof or an analogue thereof and/or wherein the composition does not comprise other protein active ingredient(s).

11. The method of treatment according to claim 1, wherein the composition is a composition in solid form which comprises from 0.0001 to 5% by mass of the protein active ingredient relative to the total mass of the pharmaceutical composition.

12. The method of treatment according to claim 1, wherein the composition is a solid form composition which comprises:
(i) 120 milligrams (mg) of monosodium phosphate dihydrate,
(ii) 1142 mg of anhydrous monosodium citrate,
(iii) 2076 mg of sodium bicarbonate,
(iv) 157 mg of sodium benzoate, and
(v) from 0.5 to 100 mg of the protein active ingredient.

13. A method for preparing a composition, said composition comprising:
(i) a protein active ingredient selected from the group consisting of GLP-1, semaglutide, liraglutide, dulaglutide, albiglutide, exenatide, and lixisenatide, and (ii) a system that can buffer the pH of the pharmaceutical composition to a value ranging from 4 to 8, wherein the system that can buffer the pharmaceutical composition comprises:

(a) from 0.5 to 20% by mass monosodium phosphate dihydrate relative to the total mass of the pharmaceutical composition, (b) from 10 to 60% by mass anhydrous monosodium citrate relative to the total mass of the pharmaceutical composition, (c) from 20 to 95% by mass sodium bicarbonate relative to the total mass of the system that can buffer the pharmaceutical composition, and (d) from 0.5 to 20% by mass sodium benzoate relative to the total mass of the pharmaceutical composition, the method comprising mixing the protein active ingredient with the system that can buffer the pH of said pharmaceutical composition to a value ranging from 4 to 8.

14. A method for the oral treatment of a disease comprising administering a kit of reagents to a subject, said kit of reagents comprising:

(i) a pharmaceutical composition in solid form comprising-a protein active ingredient, said protein active ingredient being GLP-1, semaglutide, liraglutide, dulaglutide, albiglutide, exenatide, or lixisenatide, and (ii) a pharmaceutical composition comprising a buffer system, in which said pharmaceutical composition comprising a buffer system (ii) can buffer the pH of the pharmaceutical composition comprising the protein active ingredient (i) to a value ranging from 4 to 8, when the compositions (i) and (ii) are mixed in solution and wherein the buffer system comprises:

(a) from 0.5 to 20% by mass monosodium phosphate dihydrate relative to the total mass of the pharmaceutical composition, (b) from 10 to 60% by mass anhydrous monosodium citrate relative to the total mass of the pharmaceutical composition, (c) from 20 to 95% by mass sodium bicarbonate relative to the total mass of the system that can buffer the pharmaceutical composition, and (d) from 0.5 to 20% by mass sodium benzoate relative to the total mass of the pharmaceutical composition, wherein the protein active ingredient is mixed with the buffer system, and wherein said kit of reagents is free of additional compound(s) capable of protecting the protein active ingredient of the pharmaceutical composition (i) against a degradation by digestive enzymes.

15. The method of treatment according to claim 1, wherein the protein active ingredient is semaglutide.

16. The method of treatment according to claim 7, wherein the system that can buffer the pharmaceutical composition allows to obtain a pH ranging from 5 to 7.

17. The method of treatment according to claim 16, wherein the system that can buffer the pharmaceutical composition allows to obtain a pH ranging from 6 to 7.

18. The method of treatment according to claim 17, wherein the system that can buffer the pharmaceutical composition is capable of protecting at least 75% of the protein active ingredient from degradation by at least one digestive enzyme when the pharmaceutical composition is contacted with said digestive enzyme(s).

19. The method of treatment according to claim 18, wherein the system that can buffer the pharmaceutical composition is capable of protecting at least 80% of the protein active ingredient from degradation by at least one digestive enzyme when the pharmaceutical composition is contacted with said digestive enzyme(s).

20. The method of treatment according to claim 19, wherein the system that can buffer the pharmaceutical composition is capable of protecting at least 85% of the protein active ingredient from degradation by at least one digestive enzyme when the pharmaceutical composition is contacted with said digestive enzyme(s).

21. The method of treatment according to claim 20, wherein the system that can buffer the pharmaceutical composition is capable of protecting at least 90% of the protein active ingredient from degradation by at least one digestive enzyme when the pharmaceutical composition is contacted with said digestive enzyme(s).

22. The method of treatment according to claim 21, wherein the system that can buffer the pharmaceutical composition is capable of protecting at least 95% of the protein active ingredient from degradation by at least one digestive enzyme when the pharmaceutical composition is contacted with said digestive enzyme(s).

23. The method of treatment according to claim 1, wherein the composition is a composition in solid form which comprises from 0.0001 to 5% by mass of semaglutide, relative to the total mass of the pharmaceutical composition.

24. The method of treatment according to claim 1, wherein the composition is a composition in solid form which comprises from 0.001 to 1.5% by mass of the protein active ingredient relative to the total mass of the pharmaceutical composition.

25. The method of treatment according to claim 23, wherein the composition comprises from 0.001 to 1.5% by mass of semaglutide, relative to the total mass of the pharmaceutical composition.

26. The method of treatment according to claim 1, wherein the composition is a composition in solid form which comprises from 0.001 to 1% by mass of the protein active ingredient relative to the total mass of the pharmaceutical composition.

27. The method of treatment according to claim 25, wherein the composition comprises from 0.001 to 1% by mass of semaglutide, relative to the total mass of the pharmaceutical composition.

28. The method of treatment according to claim 1, wherein the composition is a composition in solid form which comprises from 0.01 to 0.5% by mass of the protein active ingredient relative to the total mass of the pharmaceutical composition.

29. The method of treatment according to claim 27, wherein the composition comprises from 0.01 to 0.5% by mass of semaglutide, relative to the total mass of the pharmaceutical composition.

30. The method of treatment according to claim 1, wherein the composition is a composition in solid form which comprises from 0.05 to 0.5% by mass of the protein active ingredient relative to the total mass of the pharmaceutical composition.

31. The method of treatment according to claim 29, wherein the composition comprises from 0.05 to 0.5% by mass of semaglutide, relative to the total mass of the pharmaceutical composition.

32. The method of treatment according to claim 1, wherein the composition is a solid form composition which comprises:

(i) 120 milligrams (mg) of monosodium phosphate dihydrate, (ii) 1142 mg of anhydrous monosodium citrate, (iii) 2076 mg of sodium bicarbonate, (iv) 157 mg of sodium benzoate, and (v) from 0.5 to 100 mg of semaglutide.

33. The method of treatment according to claim 1, wherein the composition is a solid form composition which comprises:

(i) 120 milligrams (mg) of monosodium phosphate dihydrate, (ii) 1142 mg of anhydrous monosodium citrate, (iii) 2076 mg of sodium bicarbonate, (iv) 157 mg of sodium benzoate, and (v) from 0.5 to 40 mg of a protein active ingredient.

34. The method of treatment according to claim 1, wherein the composition is a solid form composition which comprises:

(i) 120 milligrams (mg) of monosodium phosphate dihydrate, (ii) 1142 mg of anhydrous monosodium citrate, (iii) 2076 mg of sodium bicarbonate, (iv) 157 mg of sodium benzoate, and (v) from 0.5 to 40 mg of semaglutide.

35. The method of treatment according to claim 1, wherein the composition is a solid form composition which comprises:

(i) 120 milligrams (mg) of monosodium phosphate dihydrate, (ii) 1142 mg of anhydrous monosodium citrate, (iii) 2076 mg of sodium bicarbonate, (iv) 157 mg of sodium benzoate, and (v) from 1 to 50 mg of a protein active ingredient.

36. The method of treatment according to claim 1, wherein the composition is a solid form composition which comprises:

(i) 120 milligrams (mg) of monosodium phosphate dihydrate, (ii) 1142 mg of anhydrous monosodium citrate, (iii) 2076 mg of sodium bicarbonate, (iv) 157 mg of sodium benzoate, and (v) from 1 to 50 mg of semaglutide.

37. The method of treatment according to claim 3, wherein the metabolic disease is type 2 diabetes, non-alcoholic steatohepatitis and/or obesity.

\* \* \* \* \*

SEQUENCE LISTING

```
<160> NUMBER OF SEQ ID NOS: 3

<210> SEQ ID NO 1
<211> LENGTH: 37
<212> TYPE: PRT
<213> ORGANISM: Homo sapiens
<220> FEATURE:
<223> OTHER INFORMATION: GLP-1 humaine

<400> SEQUENCE: 1

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
            35
```

-continued

```
<210> SEQ ID NO 2
<211> LENGTH: 30
<212> TYPE: PRT
<213> ORGANISM: Homo sapiens
<220> FEATURE:
<223> OTHER INFORMATION: GLP-1 (7-36) humaine

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 31
<212> TYPE: PRT
<213> ORGANISM: Homo sapiens
<220> FEATURE:
<223> OTHER INFORMATION: GLP-1 (7-37) humaine

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```